(12) United States Patent
Reinhardt

(10) Patent No.: US 7,273,464 B2
(45) Date of Patent: Sep. 25, 2007

(54) PADDED BANDAGE FOR JOINTS

(75) Inventor: Holger Reinhardt, Kempen (DE)

(73) Assignee: Bauerfeind AG, Zeulenroda (DE)

( * ) Notice: Subject to any disclaimer, the term of this patent is extended or adjusted under 35 U.S.C. 154(b) by 102 days.

(21) Appl. No.: 11/207,866

(22) Filed: Aug. 22, 2005

(65) Prior Publication Data

US 2006/0041213 A1    Feb. 23, 2006

(30) Foreign Application Priority Data

Aug. 23, 2004   (DE) .................... 10 2004 040 800

(51) Int. Cl.
*A61F 5/00* (2006.01)
*A61F 13/00* (2006.01)

(52) U.S. Cl. ................... 602/26; 602/60; 602/62; 602/63

(58) Field of Classification Search ............... 602/23, 602/20, 61, 26, 60, 63
See application file for complete search history.

(56) References Cited

U.S. PATENT DOCUMENTS

| 4,116,236 A | * | 9/1978 | Albert | 602/26 |
|---|---|---|---|---|
| 6,149,616 A | | 11/2000 | Szlema et al. | |
| 6,287,269 B1 | | 9/2001 | Osti et al. | |
| 6,520,926 B2 | * | 2/2003 | Hall | 602/64 |

FOREIGN PATENT DOCUMENTS

| DE | 83 03 118.9 U1 | 5/1983 |
|---|---|---|
| DE | 32 25 088 A1 | 12/1983 |
| DE | 38 32 438 C1 | 10/1989 |
| DE | 198 2 4649 C2 | 11/1989 |
| DE | 39 02 434 A1 | 8/1990 |
| DE | 38 38 576 A1 | 5/1991 |
| DE | 90 17 540.9 U1 | 5/1991 |
| DE | 39 91 334 C1 | 7/1992 |
| DE | 93 16 342.8 U1 | 2/1994 |
| DE | 93 17 021.1 U1 | 3/1994 |
| DE | 94 08 096.8 U1 | 9/1994 |
| DE | 43 22 028 C2 | 1/1995 |
| DE | 295 19 978 U1 | 4/1996 |
| DE | 295 19 979 U1 | 4/1996 |
| DE | 200 05 661 U1 | 9/2001 |
| DE | 200 05 663 U1 | 9/2001 |
| EP | 0 027 172 A1 | 4/1981 |
| EP | 0 262 638 A2 | 4/1988 |
| EP | 0 229 577 B1 | 4/1991 |
| EP | 0 598 291 B1 | 1/1997 |
| EP | 0 943 732 A2 | 8/1999 |
| EP | 1 338 260 A1 | 8/2003 |

* cited by examiner

*Primary Examiner*—Kim M. Lewis
(74) *Attorney, Agent, or Firm*—Birch, Stewart, Kolasch & Birch, LLP

(57) ABSTRACT

A bandage for joints wherein the bandage is made of elastic textile material and is provided with a pad. The pad is covered by an overlay of identical or similar textile material that is attached to the textile material of the bandage. The overlay covering the pad is only provided on its side facing the joint with knobs of anti-slip material thereby exerting a particular pressure on the respective parts of the joint.

4 Claims, 2 Drawing Sheets

PADDED BANDAGE FOR JOINTS

BACKGROUND OF THE INVENTION

1. Field of the Invention

The invention relates to a bandage for joints, said bandage being of elastic textile material and being provided with a pad, said pad being covered by an overlay of identical or similar textile material and being attached to the textile material of the bandage by means of edges protruding from the pad.

2. Description of Background Art

Such a bandage is described and presented in DE-PS 38 32 438. With such bandages, there is the need to fit the bandage to the joint in question in as non-slip a manner as possible. For this purpose, the textile material of the bandage has already been provided with a strip disposed in the neutral zone between the stretching and bending zones, said strip being provided with knobs of, for example, silicone, which has an anti-slip effect in relation to the skin (see DE 198 24 649 C2). A similar design is known from DE 39 02 434 A1, in which an unpadded support bandage is provided, on the skin-contacting inside of its elastic textile material, with anti-slip elements of silicone material, wherein the anti-slip elements consist of small, flat cuboids which, to that extent, have a certain similarity with knobs.

To achieve good non-slip properties, such designs require a corresponding coating of the textile material of the bandage over a large area or length in order to provide the bandage with a sufficiently secure fit.

SUMMARY AND OBJECTS OF THE INVENTION

The object of the invention is to design the initially mentioned, padded bandage for joints in such a manner that said bandage has particularly good non-slip properties. The object of the invention is achieved in that the overlay covering the pad is provided on its side facing the joint with knobs of anti-slip material.

In the padded bandage for joints according to the invention, the region of the pad is used for the required anti-slip effect, because said region projects to a certain extent out of the bandage, thereby exerting a particular pressure on the respective parts of the joint. Said pressure is used in order to provide the region of the overlay with knobs of an anti-slip material, wherein, owing to the particular contact pressure exerted by the pad on the joint in question, said knobs grip particularly effectively, thereby providing the bandage with virtually absolutely non-slip properties. Advantageously used as the anti-slip material is silicone, which can be sprayed in the liquid state onto the overlay, on which it then sets, becoming adhesively joined to the overlay.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
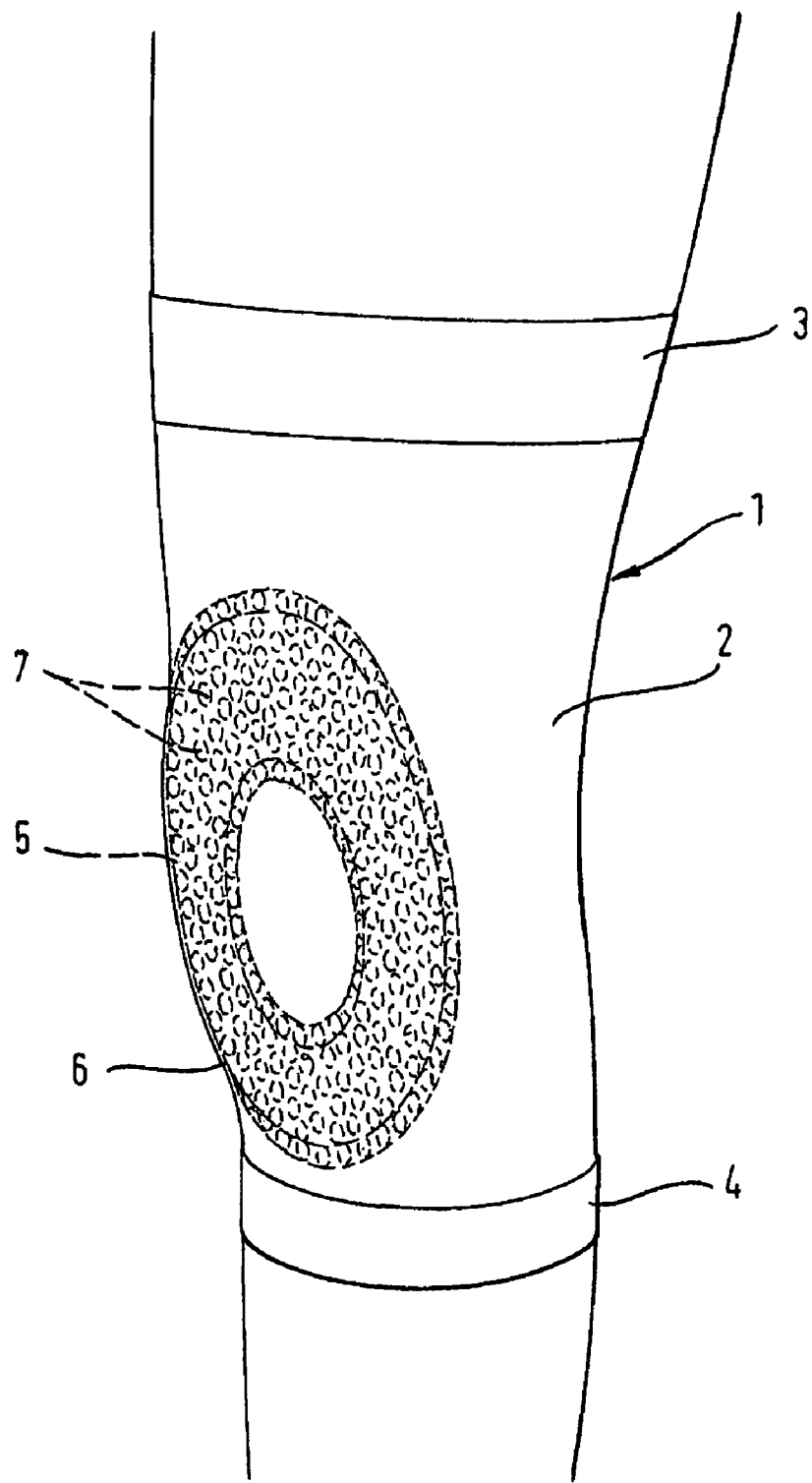
FIG. 1 shows a knee-joint bandage with ring-shaped pad surrounding the kneecap.

The bandage for joints according to the invention will now be presented with reference to the knee-joint bandage 1 shown in FIG. 1. It should, however, be pointed out that the bandage according to the invention can also be used for any other joint for which a pad integrated into the bandage is used, e.g. an elbow bandage.

The bandage 1 consists of the stocking 2 with the two terminating edges 3 and 4, which ensure in conventional manner that, in the region of said terminating edges 3 and 4, the bandage does not lead to any cutting-off of the blood supply. The bandage is provided in the region of the kneecap with the ring-shaped pad 5, which is covered by the overlay 6. The overlay 6 is attached to the textile material of the stocking 2, e.g. by means of glueing. The overlay 6 guarantees that the pad 5 is securely attached to the stocking 2 at the desired, correct place on the bandage 1.

On the side of the overlay 6 facing the joint (represented in FIG. 1 by broken lines, because not visible), the overlay 6 is provided with knobs 7 which extend over virtually the entire area of the overlay 6, wherein said knobs 7 form small, approximately hemispherical elevations, are made of silicone and, with the bandage 1 fitted to the knee joint, press against the skin of the joint, thereby guaranteeing a high degree of security against slipping, because they are pressed with particular pressure against the skin of the joint owing to the inwardly protruding pad.

Figure 2:
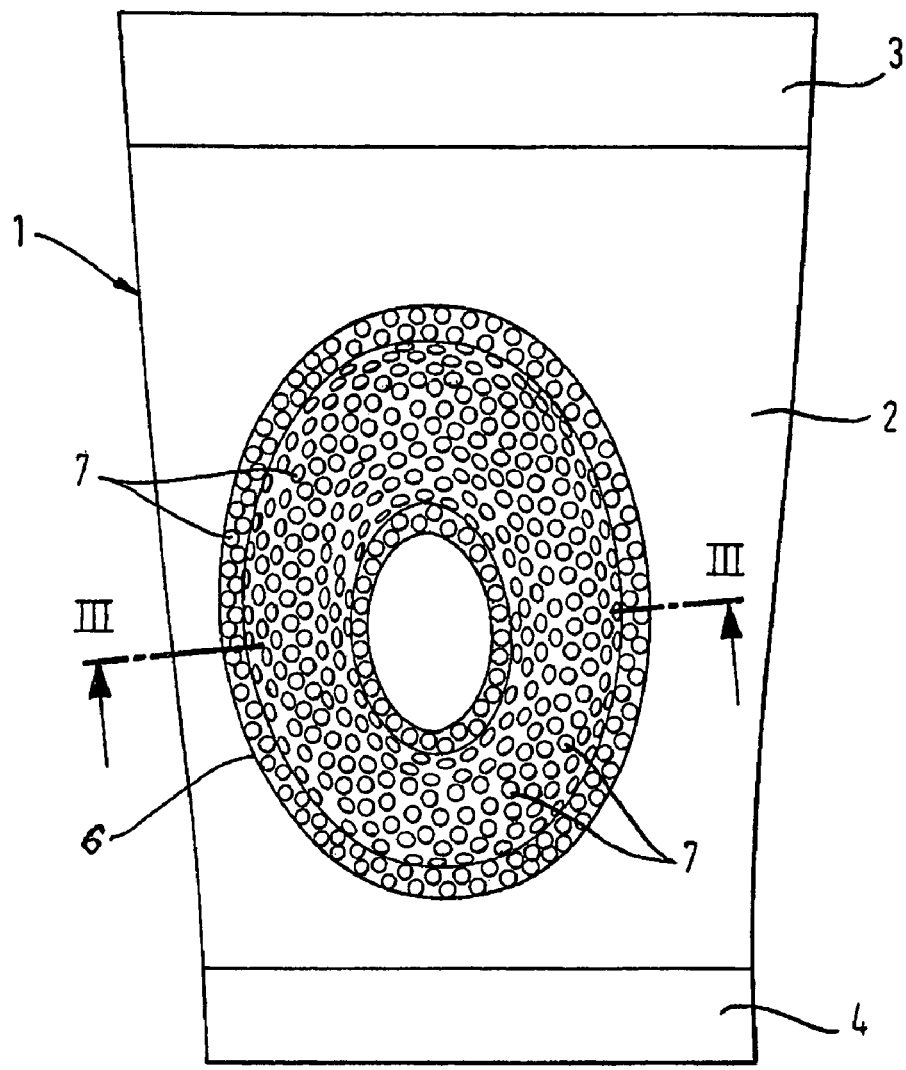
FIG. 2 shows the same bandage turned inside out, i.e. with the inside of the bandage in FIG. 1 being externally visible.

FIG. 2 shows the same knee-joint bandage, albeit with the bandage turned inside out, so that the inside during normal use is now to the outside, thereby directly allowing the observer to see the covering of the overlay 6 with the knobs 7.

Figure 3:
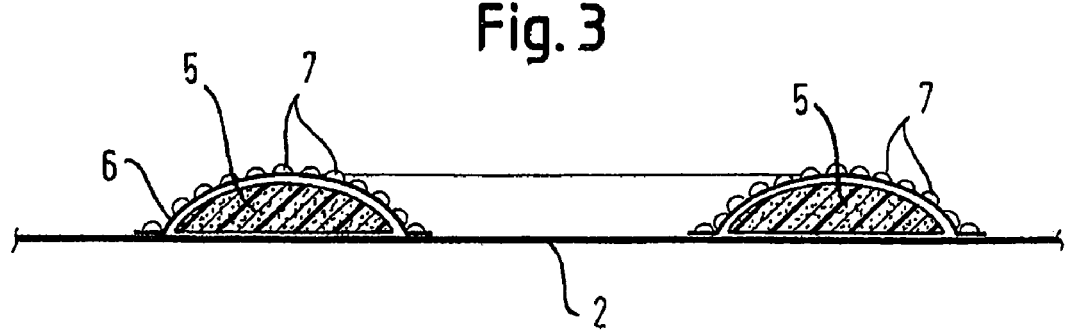
FIG. 3 shows a section along line III/III in FIG. 2.

FIG. 3 shows a section through the bandage 1 along line III-III from FIG. 2, this being a developed view, with the result that the stocking 2 appears as a straight line. As is apparent, the ring-shaped pad 5 is covered by the overlay 6, said overlay 6 being provided with the knobs 7.

On account of the particularly strong pressure of the knobs 7 against the joint, especially during bending of the joint, there is, in addition to the anti-slip effect of the knobs, also an especially intensive massage effect on that region of the joint which is covered by the knobs, this being additionally desired in particular cases.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. Bandage (1) for joints, said bandage (1) being of elastic textile material and being provided with a pad (5), said pad (5) being covered by an overlay (6) of identical or similar textile material and being attached to the textile material of the bandage (1), characterized in that the overlay (6) covering the pad (5) is only provided on its side facing the joint with knobs (7) of anti-slip material thereby exerting a particular pressure on the respective parts of the joint.

2. Bandage for joints according to claim 1, characterized in that silicone is used as the anti-slip material.

3. Bandage for joints according to claim 1, characterized in that the knobs (6) are sprayed in the liquid state onto the overlay and set thereon while becoming adhesively joined to the overlay.

4. Bandage for joints according to claim 2, characterized in that the knobs (6) are sprayed in the liquid state onto the overlay and set thereon while becoming adhesively joined to the overlay.

* * * * *